(12) United States Patent
Kavusi et al.

(10) Patent No.: US 9,927,435 B2
(45) Date of Patent: Mar. 27, 2018

(54) MULTISITE BIOSENSOR AND ASSOCIATED METHOD

(75) Inventors: Sam Kavusi, Menlo Park, CA (US);
Daniel Roser, St. Georgen (DE);
Christoph Lang, Cupertino, CA (US);
AmirAli Haj Hossein Talasaz, San Francisco, CA (US)

(73) Assignees: Robert Bosch GmbH, Stuttgart (DE);
Office of Technology Licensing—Stanford University, Palo Alto, CA (US)

( * ) Notice: Subject to any disclaimer, the term of this patent is extended or adjusted under 35 U.S.C. 154(b) by 780 days.

(21) Appl. No.: 12/580,113

(22) Filed: Oct. 15, 2009

(65) Prior Publication Data

US 2011/0091870 A1    Apr. 21, 2011

(51) Int. Cl.
*G01N 33/00* (2006.01)
*G01N 33/543* (2006.01)
(Continued)

(52) U.S. Cl.
CPC ....... *G01N 33/54393* (2013.01); *G01N 29/32* (2013.01); *G01N 33/53* (2013.01); *G01N 33/543* (2013.01); *G01N 33/54366* (2013.01)

(58) Field of Classification Search
USPC ....... 73/826.046; 356/478; 435/288.3, 288.4, 435/7.1; 436/174–180, 501, 518,
(Continued)

(56) References Cited

U.S. PATENT DOCUMENTS

| 5,501,987 A | 3/1996 | Ordonez et al. |
| 7,087,373 B2 * | 8/2006 | Xie et al. ................ 435/4 |

(Continued)

FOREIGN PATENT DOCUMENTS

| CA | 2413978 C | 12/2008 |
| EP | 0574782 A2 | 12/1993 |

(Continued)

OTHER PUBLICATIONS

Edman et al., Electric field directed nucleic acid hybridization on microchips, 1997, Nucleic Acids Research, vol. 25, No. 24, pp. 4907-4914.*

(Continued)

*Primary Examiner* — Erik B Crawford
(74) *Attorney, Agent, or Firm* — Maginot Moore & Beck LLP

(57) ABSTRACT

A method of detecting a biomarker in one embodiment includes identifying a quantity of biomolecule types in a sample, exposing the sample to a plurality of test sites, wherein the number of test sites in the plurality of test sites is equal to or greater than the identified quantity of biomolecule types, establishing, for each of the plurality of test sites, a respective test environment, wherein the test environment for each of the plurality of test sites is different from the test environment for each of the other of the plurality of test sites, obtaining a detection signal associated with each of the plurality of test sites, and determining the concentration of one of the biomolecule types based upon the obtained detection signals.

18 Claims, 8 Drawing Sheets

(51) Int. Cl.
*G01N 29/32* (2006.01)
*G01N 33/53* (2006.01)

(58) Field of Classification Search
USPC .......................................... 436/523–536, 809
See application file for complete search history.

(56) References Cited

U.S. PATENT DOCUMENTS

| | | | |
|---|---|---|---|
| 7,892,854 B2 * | 2/2011 | Banerjee et al. | 436/525 |
| 2003/0198967 A1 * | 10/2003 | Matson et al. | 435/6 |
| 2003/0232399 A1 | 12/2003 | Robertson et al. | |
| 2006/0019299 A1 | 1/2006 | Kang et al. | |
| 2006/0108236 A1 | 5/2006 | Kasielke et al. | |
| 2007/0097364 A1 | 5/2007 | Shepard et al. | |
| 2009/0061535 A1 * | 3/2009 | Dowd et al. | 436/518 |

FOREIGN PATENT DOCUMENTS

| | | |
|---|---|---|
| JP | H09-304393 A | 11/1997 |
| JP | 2002-272498 A | 9/2002 |
| JP | 2004-061262 A | 2/2004 |
| JP | 2005-172807 A | 6/2005 |
| WO | 199014806 | 12/1990 |
| WO | WO 2007062666 A1 * | 6/2007 |
| WO | 2007127981 A2 | 11/2007 |

OTHER PUBLICATIONS

Asanov et al., Regenerable Biosensor Platform: A Total Internal Reflection Flourescence Cell with Electrochemical Control; Analytical Chemistry, vol. 70, No. 6, pp. 1156-1163, 1998, (8 pages).
Heaton et al., Electrostatic surface plasmon resonance: Direct electric field-induced hybridization and denaturation in monolayer nucleic acid films and label-free discrimination of base mismatches, Proceedings of the National Academy of Sciences of the U.S.A., vol. 98, No. 7, pp. 3701-3704, 2001, (4 pages).
Jackola et al., Entropy-favored human antibody binding reactions with a non-infectious antigen, Molecular Immunology 45, pp. 1494-1500, 2008 (7 pages).
Liron et al., Voltage-induced inhibition of antigen-antibody binding at conducting optical waveguides, Biosensors and Bioelectronics, 17, pp. 489-494, 2002 (6 pages).
Roy et al., Effect of pressure on antigen-antibody complexes: modulation by temperature and ionic strength, Molecular Immunology 36, pp. 1149-1158, 1999 (10 pages).
Selby, Interference in immunoassay, Annals of Clinical Biochemistry, 36, pp. 704-721, 1999 (18 pages).
Wong et al., Dynamic control of biomolecular activity using electrical interfaces, The Royal Society of Chemistry, 3, pp. 267-274, 2007 (8 pages).
O'Connor T et al: "The dependence of radioimmunoassay detection limits on antibody affinity", Journal of Immunological Methods, Elsevier Science Publishers B.V., Amsterdam, NL, vol. 208, No. 2, Oct. 27, 1997, pp. 181-189, XP004158712, (9 pages).
Jeney C et al: "Taguchi optimisation of Elisa procedures", Journal of Immunological Methods, Elsevier Science Publishers B.V., Amsterdam, NL, vol. 223, No. 2, Mar. 4, 1999, pp. 137-146, XP0044158712, (10 pages).
English Translation of Chinese Second Office Action and Search Report corresponding to Chinese Patent Application No. 201080051665.5, dated Aug. 12, 2014 (10 pages).
English Translation of Japanese Notice of Rejection corresponding to Japanese Patent Application No. 2012-534315, dated Nov. 14, 2014 (4 pages).
English Translation of KIPO Notice of Preliminary Rejection corresponding to Korean Patent Application No. 10-2012-7012355 (11 pages).

* cited by examiner

MULTISITE BIOSENSOR AND ASSOCIATED METHOD

FIELD

This invention relates to diagnostic tests and more specifically to affinity based diagnostic tests.

BACKGROUND

Diagnostic tests that can be performed at the point of care of an individual, such as at the bedside of a patient, at a care provider location, or at the home of the patient, are becoming increasingly popular. Diagnostic tests include tests directed to identifying biomarkers such as Nucleic Acid, protein, and small molecules. Many of the diagnostic testing devices incorporate affinity based sensors which are considered to be the state-of-the-art in detection of biomarkers.

Affinity based biosensors function according to a "key-lock" principal in which a molecule with very high association factor to the biomarker of interest is used for detection. For example, a pregnancy test kit may incorporate a monoclonal antibody specific to a β-subunit of hCG (βhCG). The antibody is conjugated with a tag, e.g., gold, latex, or fluorophore, which is used for detection. If the targeted molecule binds with the conjugated antibody, the tagged key-lock pair will be detectable such as by a visible test line.

ELISA plates and microarrays (e.g., Nucleic Acid, peptide, and protein) incorporate a similar principal. FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample including molecules of interest 18 is then added to the well in which the primary antibody 12 is immobilized. Next, the sample is incubated for some time. During incubation, the blocker 16 prevents the molecules of interest in the sample from binding to the surface of the substrate 14 in order to avoid false binding. During incubation, some of the molecules of interest 18 become bound with some of the antibodies 12 as depicted in FIG. 2. After incubation, the remaining sample is washed to remove the unbound molecules of interest 18.

Subsequently, a secondary antibody 20 with a bound label 22 is added to the well, incubated, and washed resulting in the configuration of FIG. 3. As depicted in FIG. 3, the labeled secondary antibodies 20 are bound to the molecules of interest 18 that are in turn bound to the antibodies 12. Accordingly, the number of labels 22 bound by the antibodies 20 to the molecules of interest 18 is proportional to the concentration of the target antigen. Depending on the label used, the number of labels can be finally detected using colorimetry, amperometry, magnetometry, voltammetry, luminescence, or fluorescence detection. Other label-free antibody processes such as surface plasmon resonance may alternatively be used.

The two main figures-of-merit in a detection assay include sensitivity and cross-reactivity; both of which affect the minimum detectable concentration and the diagnosis error rate. The sensitivity in such tests is generally limited by label detection accuracy, association factor of the antibody-antigen pair, and the effective density of the probe antibody on the surface.

One issue that arises with affinity based sensors is the cross-reactivity of the sensor to other biomarkers. In other words, rather than sensing a single biomarker or molecule of interest, a sensor tends to also sense biomarkers other than the biomarker of interest. The cross-reactivity issue is depicted in FIG. 4 wherein an ELISA assay 30 includes antibodies 32 immobilized on a substrate 34 with a blocker 36 coating most of the surface of the substrate 32. Additionally, a labeled secondary antibody 38 is bound to a molecule of interest 40 which is in turn bound by the primary antibody 32. The labeled secondary antibody 38 has also bound to a molecule 42 which exhibited an affinity for the primary antibody 32 and to the labeled secondary antibody 38. The sensitivity to a broad range of biomarkers thus increases the false negative/positive rate of diagnostic tests at clinical level as reported, for example, by P. A Benn et al., "Estimates for the sensitivity and false-positive rates for second trimester serum screening for Down syndrome and trisomy 18 with adjustment for cross identification and doublepositive results," *Prenatal Diagnosis*, Vol. 21, No. 1, pp 46-51, 2001. The presence of other molecules (secondary molecules or antigens) in the sample thus affects the minimum detectable concentration by binding to the primary antibody.

The accuracy of the assay may further be affected by physiosorption. As further depicted in FIG. 4, some features 44 present in the ELISA assay 30, either contaminants or simply an incongruity, may also be bound to a labeled secondary antibody 38. The physiosorbed labeled secondary antibody 38 thus causes an increased background signal.

In an effort to mitigate the various sensitivity and interference issues involved with affinity based testing, a particular assay is typically optimized by finding a combination of reagents and environmental conditions that maximizes the binding of the molecule of interest to the antibody. Thus, optimization can entail incorporating highly selective antibodies.

Overcoming the cross-reactivity and background problems can significantly delay development of a new assay test and can increase the cost and complexity of the overall test. For example a typical development of an ELISA assay requires several scientists working for more than a year to identify an acceptable antibody. Cross-reactivity of proteins is a common source of the failure of such development efforts.

The issue of broad biomarker sensitivity can also be mitigated by incorporating a number of different affinity based sensors into a test device and then determining the relative concentrations of biomarkers. This approach, however, increases the cost of manufacturing the test device and the costs associated with processing the test device.

A need exists for a device and method of performing an assay incorporating low cost antibodies. A further need exists for low cost assays including multiplexed assays, protein arrays, lateral flow devices, sandwich assays, competitive assays, or bead based arrays which provide accurate results and a method of using such arrays. Methods and devices which provide more accurate results than so-called optimized assays would be a further benefit.

SUMMARY

In accordance with one embodiment, a method of detecting a biomarker includes identifying a quantity of biomolecule types in a sample, exposing the sample to a plurality of test sites, wherein the number of test sites in the plurality of test sites is equal to or greater than the identified quantity of biomolecule types, establishing, for each of the plurality of test sites, a respective test environment, wherein the test environment for each of the plurality of test sites is different from the test environment for each of the other of the plurality of test sites, obtaining a detection signal associated with each of the plurality of test sites, and determining the concentration of one of the biomolecule types based upon the obtained detection signals.

In accordance with another embodiment, a method of determining a concentration of a biomarker in a sample includes identifying a quantity of detection signal contributors for a plurality of detection signals, wherein at least one of the detection signal contributors is a molecule of interest, exposing a sample to a plurality of test sites, wherein the number of test sites in the plurality of test sites is equal to or greater than the identified quantity of detection signal contributors, establishing, for each of the plurality of test sites, a respective test environment, wherein the test environment for each of the plurality of test sites is different from the test environment for each of the other of the plurality of test sites, obtaining a respective one of the plurality of detection signals from each of the plurality of test sites, and determining the concentration of a biomolecule of interest based upon the obtained plurality of detection signals.

DESCRIPTION

Figure 1:
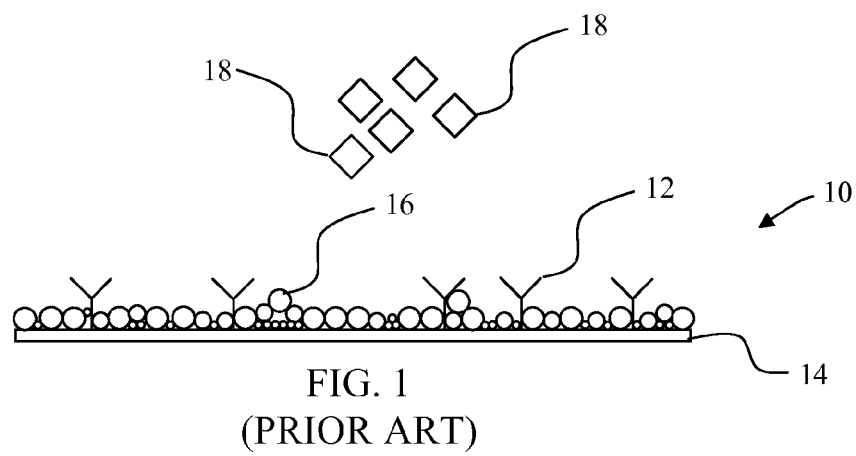
FIG. 1 depicts a schematic of a prior art test site within an ELISA array with an antibody and blockers formed on a substrate as a sample is added to the test site.
Figure 2:
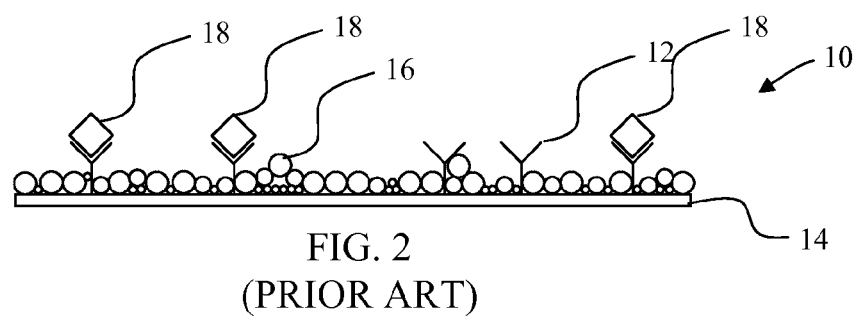
FIG. 2 depicts the test site of FIG. 1 with a molecule of interest bound to some of the antibodies of FIG. 1 after the test site has been incubated and washed.
Figure 3:
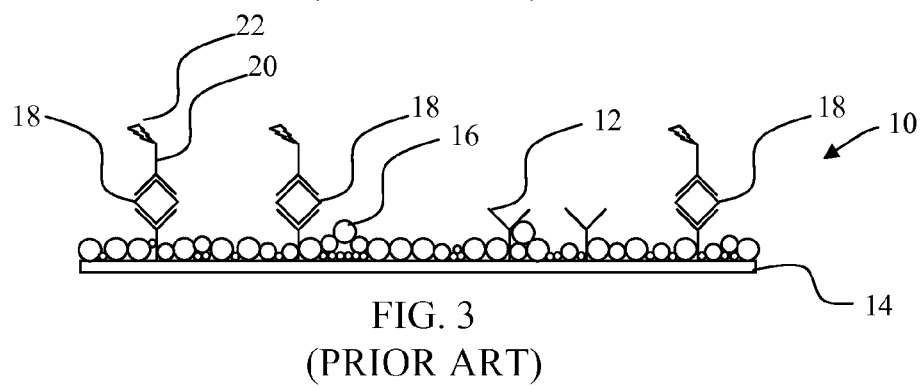
FIG. 3 depicts the test site of FIG. 2 after a labeled secondary antibody has been added and the test site has again been incubated and washed so that the labeled secondary is bound to the bound molecules of interest.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
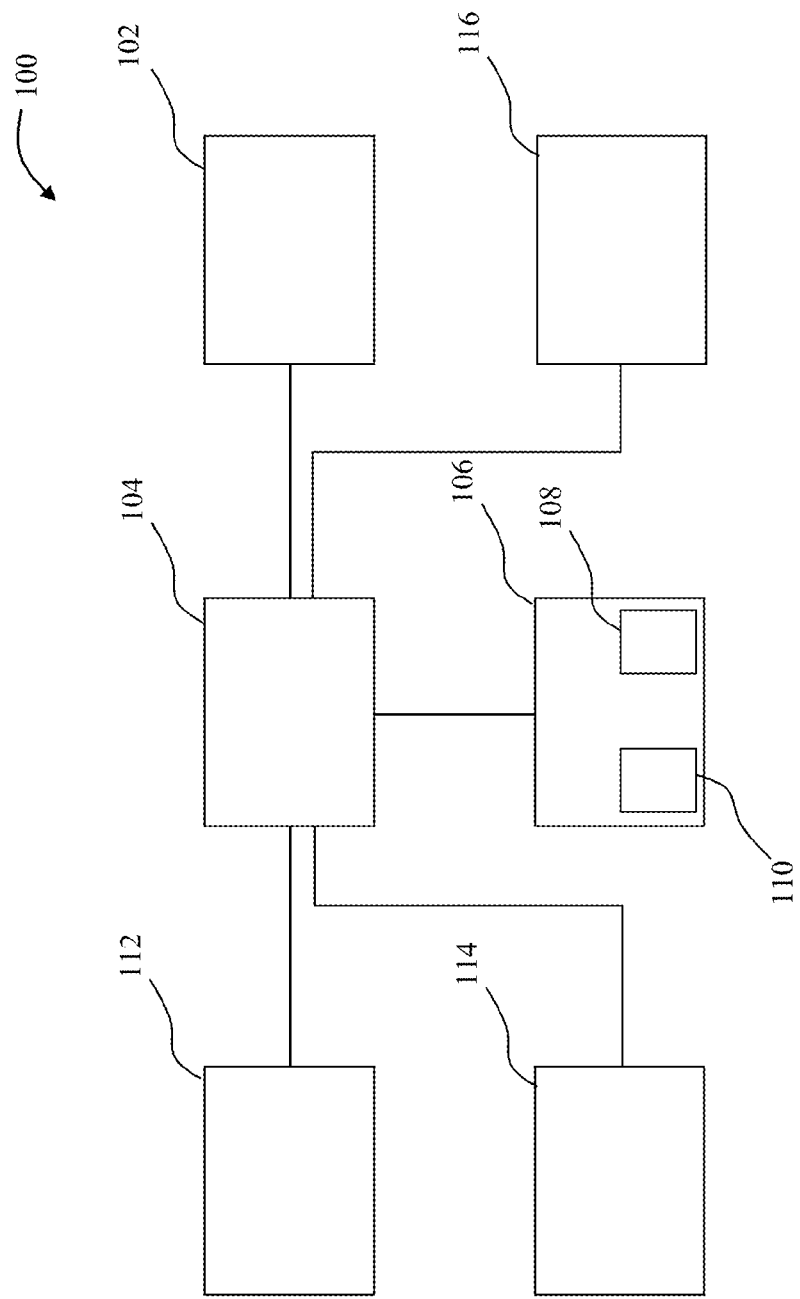
FIG. 5 depicts a multi-site biosensor system configured to expose a single sample to different environmental conditions allowing determination of the concentration of a molecule of interest in a sample including other molecules which increase the detected signal.

Referring to FIG. 5, there is depicted a representation of a multisite biosensor system generally designated 100. The biosensor system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the biosensor system 100, and that allow internal information of the biosensor system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components as appropriate. Affinity databases 110 are also located within the memory 106.

Figure 6:
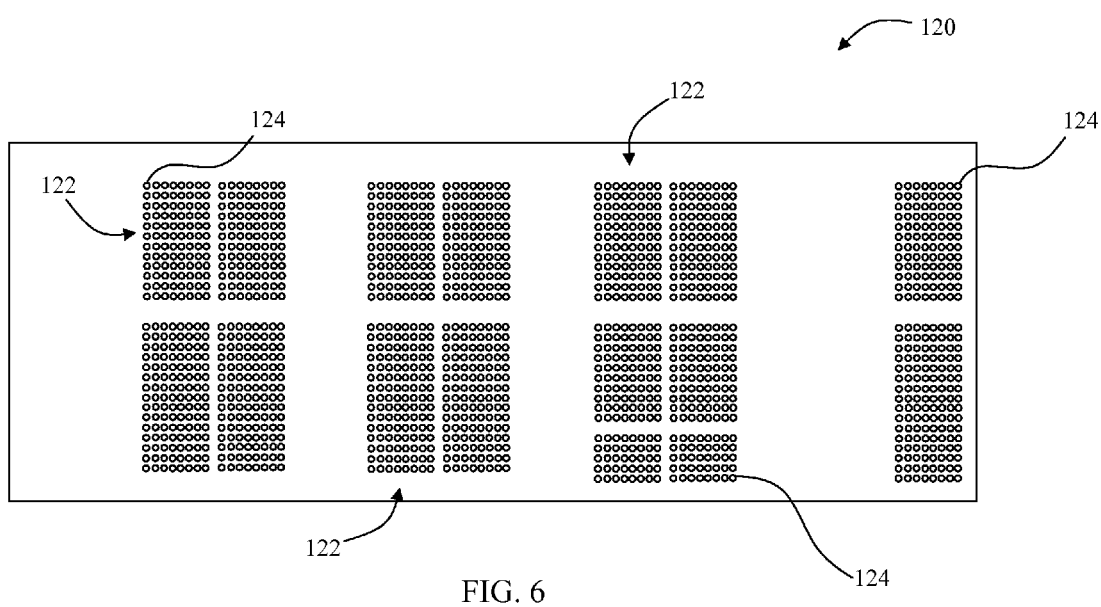
FIG. 6 depicts a platform for providing a number of different test sites in the form of a microarray.

The biosensor system 100 further includes environment control equipment 112 and environment detector suite 114. The environment control equipment 112 is configured to establish and maintain environmental conditions, in this example, within a microarray 120 depicted in FIG. 6. Various methods may be used to form the microarray platform 120. By way of example, U.S. Pat. No. 5,807,522 discloses a method for forming microarrays. The microarray platform 120 includes a number of different subarrays 122. The subarrays 122 include a number of test sites 124. The number of subarrays 122 as well as the number of test sites 124 within each of the subarrays 122 may be varied within the scope of the invention. In this embodiment, the environment control equipment 112 is operable to establish a temperature profile within the microarray platform 120. The precise temperature within each of the test sites 124 may be detected by the detector suite 114.

The system 100 further includes a label reader 116. The label reader 116 may be included in a single device along with the other components of the system 100. Alternatively, one or more of the components of the system 100 may be provided as a separate device which may be remotely located from the other components of the system 100.

The test sites 124 are prepared with a capturing agent effective for capturing a biomolecule of interest. Further details regarding the biosensor system 100 are provided with reference to the procedure 130 of FIG. 7. The processor 104 executes the program instructions 108 to execute at least some of the procedure 130 of FIG. 7. In different embodiments, the procedure 130 may be modified to include more or fewer steps depending upon the specific criterion.

At block 132, a molecule of interest is identified and then an antibody with an affinity for the molecule of interest is identified (block 134). A binding efficiency coefficient for the molecule of interest ($\alpha_i$) with the identified antibody is then identified for at least two different environmental conditions (block 136) and stored in one of the affinity databases 110 (block 138).

Potential sources of test signal interference or noise likely to be present in a tested sample are then identified (block 140). The identification of signal interference may include, for example, an identification of likely or potential molecules within a sample that also have an affinity for the identified antibody. A binding efficiency coefficient for each source of noise ($\alpha_n$) with the identified antibody is then identified for each of the different environmental conditions (block 142) and stored in one of the affinity databases 110 (block 144).

At block 146, the microarray platform 120 is prepared by depositing the desired amount of the selected capturing agent in each of the test sites 124. In alternative embodiments, a subset of the test sites 124 may be prepared with a first capturing agent while another subset of the test sites 124 may be prepared with a second capturing agent so as to allow two separate tests to be conducted within a single microarray platform 120. Additional configurations within a single microarray platform 120 may also be used. By way of example, each of the test sites within one of the subarrays 122 may be prepared with the same capturing agent while each of the subarrays 122 includes a different capturing agent. The number of test sites 124 prepared with a particular capturing agent in this embodiment is selected to be at least the same as the number of noise sources identified above plus the molecule of interest.

Once the microarray platform 120 is prepared, a sample is introduced into the selected set of test sites 124 (block 148). If not already established, the environment within each of the selected set of test sites 124 is controlled to establish, within each of the selected set of test sites 124, a different test environment (block 150). In this example, the environmental condition that is controlled is temperature. Accordingly, a thermal profile is established across the microarray platform 120. Depending upon the particular embodiment, this may be accomplished by providing a unique heater/cooler for each of the selected set of test sites 124 or subarrays 122. In other embodiments, heat is applied at one end of the microarray platform 120 and a heat sink is thermally attached to the opposite end of the microarray platform 120 to establish a thermal gradient across the microarray platform 120.

The sample is then incubated at the established test environment for a predetermined time (block 152). During the incubation, the actual test environment within each of the selected set of test sites 124 is monitored by the environment detector suite 114 and data indicative of the established test environment is provided to the processing circuit 104 (block 154). When the sample has been sufficiently incubated, the test sites 124 are washed (block 156) and a labeled secondary antibody is introduced into the selected set of test sites 124 (block 158) and incubated (block 160). The selected set of test sites 124 are then washed (block 162) and the labels remaining in the test sites 124 are detected by the label reader 116 (block 164). Based upon the signals associated with the number of labels remaining in the selected set of test sites 124, the concentration of one or more molecules of interest within the sample is calculated by the processing circuit 104.

Figure 8:
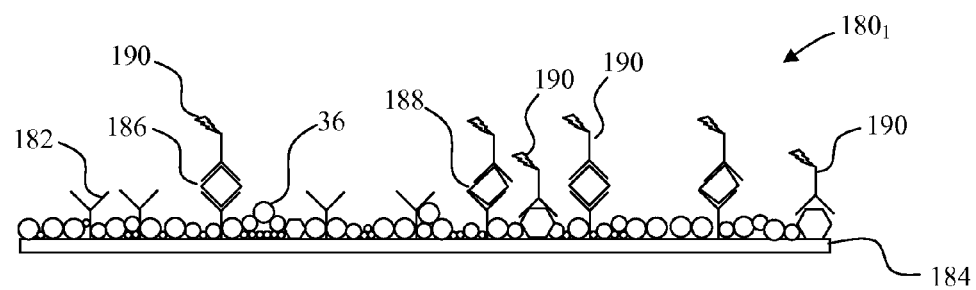
FIG. 8 depicts a schematic of a test site wherein a labeled secondary is bound to molecules of interest, to interfering molecules due to cross-reactivity, and also physiosorbed to the surface of the substrate raising the background noise level of the test.

Calculation of the concentration of one or more molecules of interest is possible since the signal obtained by the label reader 116 for a particular one of the selected set of test sites 124 is the summation of the contributors to the signal including the molecule of interest, and each of the noise sources such as interfering molecules. By way of example, FIG. 8 depicts a test site $180_1$ including antibodies 182 formed on a substrate 184. Antigen 186 has been bound to some of the antibodies 182. Some interfering antigen 188 has also bound to some of the antibodies 182. A labeled secondary antibody 190 has bound to each of the bound antigens 186 and each of the bound interfering antigens 188. Some of the labeled secondary antibody 190 has also physiosorbed to the blocked surface of the substrate 184.

The relative proportion of the signal attributable to each of the contributors is dependent upon the concentration of the particular contributor, the concentration of the other contributors, and the relative affinity to the initially deposited capturing agent of each of the contributors. The relationship is reflected in the following equation:

$$S_1 = \alpha_{1-1}C_1 + \alpha_{1-2}C_2 + \ldots \alpha_{1-x}C_x$$

wherein $S_1$ is the signal associated with the detected label in the spot $122_1$, $\alpha_{1-1}$ is the binding efficiency proportional to affinity for the identified contributor (1 through x) at the environment established in spot $122_1$, and C is the concentration in the sample of the identified contributor (1 through x).

Figure 9:
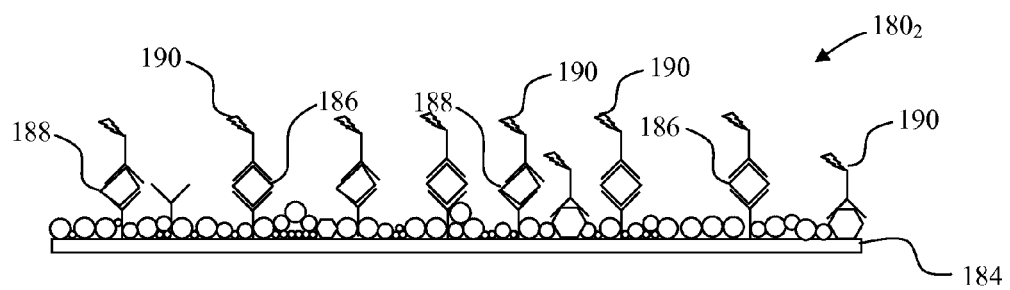
FIG. 9 depicts a schematic of a test site formed identically to the test site of FIG. 8 and exposed to the same sample to which the test site of FIG. 8 was exposed, but maintained at a temperature different from the temperature of the test site of FIG. 8 during incubation, resulting in different binding efficiencies for the different signal contributors.

Accordingly, because the number of the selected set of test sites 124 is equal to at least the number of interfering contributors plus one, the number of detected signals will correspond to the number of identified interfering contributors plus the molecule of interest. The contribution of the various sources to the overall signal, as well as the value of the overall signal, will vary from test site to test site. For example, FIG. 9 depicts a test site $180_2$ which was prepared identically to the test site $180_1$ and exposed to a sample identical to the sample used with the test site $180_1$. The test environment in each of the test sites $180_x$ was different. Accordingly, the labeled secondary antibody 190 bound to the molecule of interest has increased from two in FIG. 8 to four in FIG. 9. Additionally, the labeled secondary antibody 190 bound to the interfering antigen has increased from two in FIG. 8 to three in FIG. 9.

Thus, if three noise contributors are identified in a sample, such as analytes that bind non-specifically to primary antibody sites and prevent the biomarker to bind, analytes that form a sandwich and produce erroneous signals, and analytes that physiosorb to the surface of the test site and produce erroneous signals, along with the molecule of interest, four test sites, such as four of the test sites 124, are the minimum number of cells prepared at block 144. Therefore, four signals will be obtained, as reflected in the following equations:

$$S_1 = \alpha_{1-1}C_1 + \alpha_{1-2}C_2 + \alpha_{1-3}C_3 + \alpha_{1-4}C_4$$

$$S_2 = \alpha_{2-1}C_1 + \alpha_{2-2}C_2 + \alpha_{2-3}C_3 + \alpha_{2-4}C_4$$

$$S_3 = \alpha_{3-1}C_1 + \alpha_{3-2}C_2 + \alpha_{3-3}C_3 + \alpha_{3-4}C_4$$

$$S_4 = \alpha_{4-1}C_1 + \alpha_{4-2}C_2 + \alpha_{4-3}C_3 + \alpha_{4-4}C_4$$

Each term is thus proportional to a binding efficiency factor, α, which is a function of the molecule affinities and other assay conditions, e.g., mass transport. Accordingly, because the same sample is used in each of the test sites 124, and because the binding efficiency of the molecule of interest and the interfering antigens for the specific environment in each of the test sites 124 is known, the procedure 130 provides four equations and four unknowns. The concentrations of each of the contributors can thus be ascertained in a known manner. Accordingly, the concentrations of multiple molecules of interest within a sample can also be ascertained. In practice the signals are noisy and linear estimation algorithms may be used to estimate the value used for any particular signal. Additionally, one or more sensor sites may be used as a control site to improve the accuracy of the procedure 130.

An important consideration in selecting the environmental factor(s) controlled at block 148 is ensuring that the binding efficiency factors for each of the contributors do not exhibit a linear change compared with the binding efficiency factors for the other contributors for the different environments selected for each of the selected set of test sites 124. An environmental factor which results in large differences in binding efficiency between the signal contributors in a sample will improve accuracy. Optimally, a single environmental factor will provide sufficient differences in binding efficiencies. If needed, however, multiple factors may be modified in various combinations to provide sufficient data to resolve the unknown quantities. As additional factors are included, the minimum number of test sites and the complexity of the subsequent computations are also increased.

In the foregoing example, the temperature within each of the test sites 124 was controlled to provide different binding efficiencies. In embodiments incorporating CMOS technology, a temperature gradient within the chip can be established using on-chip resistors such as polysilicon resistors or integrated Peltier elements. Low power on-chip temperature sensors can be used to accurately measure the temperature within each of the test sites. A multisite biosensor can thus be implemented on a printed circuit board, glass, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The chip can be part of a system using stand alone microfluidics or a capillary principle or may used with a separately provided device. The signal estimation and the assay data can be hard coded on the CMOS chip if desired.

Temperature is not the only environmental factor which can be used to establish different test environments. The electric field in which incubation is conducted has been shown to modify the binding efficiencies of molecules as reported by F. A. Armstrong, "Recent developments in dynamic electrochemical studies of adsorbed enzymes and their active sites," *Current Opinion in Chemical Biology*, Vol. 9, No. 2, pp 110-117, 2005, R. J. Heaton et al., "Electrostatic surface plasmon resonance: direct electric field-induced hybridization and denaturation in monolayer nucleic acid films and label-free discrimination of base mismatches," *Proceedings of National Academy of Science*, Vol. 98, No. 7, pp. 3701-3704, 2001, and I. Wong et al., "Dynamic control of biomolecular activity using electrical interfaces," *Soft Matter*, Vol. 3, No. 3, pp 267-274, 2007.

In some embodiments, the electric field within each of the test sites may be controlled to be different from the electric field within each of the other of the test sites. The electric field can be used to modify, e.g., local concentrations, PH, etc. The underlying mechanisms include electrolysis and ion attraction. The use of an AC signal may further provide local mixing by creating movement of ions within the sample, e.g., through electrohydrodaynamic effects. Many voltage ranges which provide the foregoing effects are CMOS compatible. Accordingly, a CMOS chip with surface electrodes may be used. Depending upon the desired effect, one, two or more electrodes may be provided at a particular test site and either exposed or isolated from the test sample. Another fabrication method incorporates glass slides with electrodes (e.g., ITO, gold) or plastic or paper membrane with printed electrodes (e.g., carbon, gold, silver).

Another approach to controlling the test environment is through the use of magnetic beads and a controlled magnetic field. The magnetic beads are functionalized with molecules that have high affinity against a range of biomolecules, e.g., antibody, Nucleic Acid, or aptamers. As the magnetic beads are moved across the sensor sites, different molecules will bind to them at different rates, thereby scraping the surfaces of the test sites and "cleaning" the test sites. Controlling the magnetic field within the test sites affects the extent of "cleaning" that occurs at each test site, thereby modifying the binding efficiency of different molecules depending upon the strength of the bonds formed between the molecules and the antibodies. An external magnet may be used in various embodiments to bias the magnetic field to the desired values since CMOS integrated coils can only generate moderate magnetic fields.

A further embodiment used to establish different test environments incorporates multiple capturing agents in preparing the test sites. By changing the relative concentration of the capturing agents, the binding efficiencies for the contributors in a particular sample can be changed in each of the test sites. The recipe for the capturing agents in each of the test sites may be different antibodies, aptamers, Nucleic Acid, or other biomolecules. Thus, so long as sufficient changes in efficiencies between at least two contributors can be affected by modification of the relative concentration of a capturing agent, the capturing agent may be useful even if the capturing agent is not very specific.

A similar embodiment achieves changes in the binding efficiencies of one or more contributors by a recipe with a modification of the concentration of a single capturing agent between multiple sites. Another approach is to modulate the affinities using different pressure at different test sites while washing the spots. Pressure modification can be achieved in a fluidic setup.

The type of sensor or sensors incorporated into the label reader 116 will vary depending upon the particular label used. Various embodiments may thus use luminescence, fluorescence, colorimetric, electrochemical, impedance, and magnetic sensors. The sensors should be configured to allow isolation of the signal produced by a selected one or more test sites. Likewise, the sensors incorporated into the environment detector suite 114 may include IR sensors, and Hall sensors. AMR sensors or GMR sensors may be provided to monitor the density of magnetic beads on a test site surface. ISFETs or CMOS based charge detection circuits may be used in electrochemical embodiments.

The effectiveness of the procedure 130 was verified using a simulation model based upon parameters extracted from an experiment with mouse anti-streptavidin monoclonal antibody and rabbit anti-streptavidin polyclonal antibody. In the simulation, the two different antibodies were differentiated by modulating the affinities of the antibodies at two different test sites by establishing two different temperatures at the two test sites while using the same labels and same capture molecule at both test sites.

Figure 10:
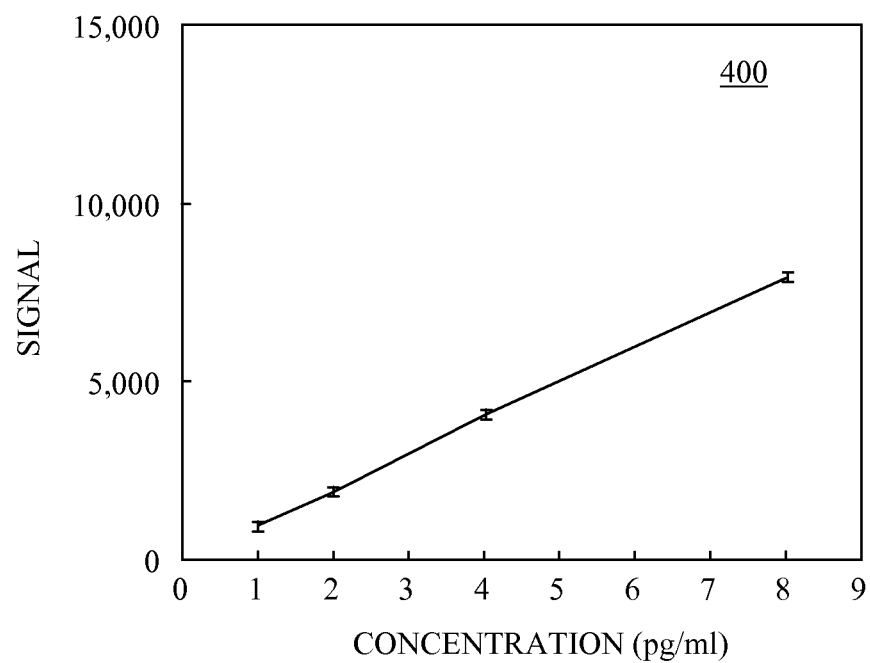
FIG. 10 depicts a graph of a modeled detected signal for samples of different concentrations of a molecule of interest showing a linear increase in the detected signal as the concentration of the molecule of interest in the samples increases.

Initially, the detected signal for varying concentrations of an AB diamond antibody was derived. The results of the signal from pure samples of the AB diamond antibody are depicted in the graph 400 of FIG. 10. The graph 400 indicates that as the concentration of the AB diamond antibody was increased from 1, to 2, to 4, and then to 8 pg/ml, the detected signal increased in a substantially linear fashion.

Figure 11:
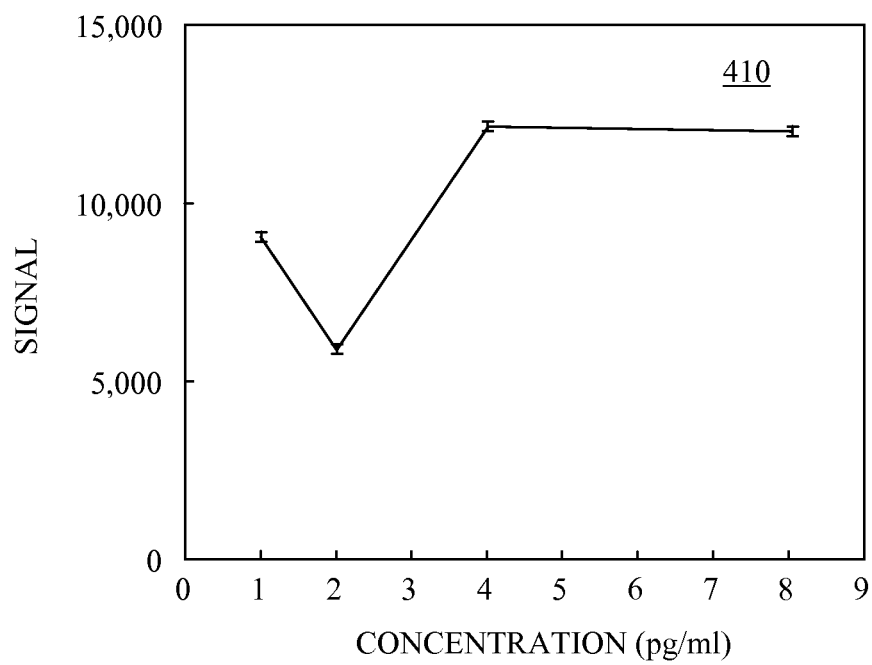
FIG. 11 depicts a graph of the modeled detected signal for samples of different concentrations of a molecule of interest, and another molecule which increases the detected signal, showing the signal resulting from the molecule of interest to be masked by the signal resulting from the other molecule.

FIG. 11 depicts a graph 410 of the signal obtained when the AB diamond antibody was increased from 1, to 2, to 4, and then to 8 pg/ml in the presence of an AB circle antibody of varying concentrations. The AB diamond antibody and the AB circle antibody exhibited similar binding efficiencies at the temperature selected for the modeling which resulted in the graph 410. As the AB diamond antibody was increased from 1, to 2, to 4, and then to 8 pg/ml the concentration of the AB circle antibody was varied from 8, to 4, to 8, and back to 4 pg/ml, respectively. The graph 410 indicates that the presence of the AB circle antibody masked the signal resulting from the AB diamond antibody.

Within the simulation, the binding efficiency of the AB diamond antibody and the AB circle antibody were modeled with a 6% error, for two different temperatures. The binding efficiency of the AB diamond antibody, normalized to the binding efficiency at a first test site, was reduced to 0.6 at a second test site. The binding efficiency of the AB circle antibody, normalized to the binding efficiency at the first test site, was reduced to 0.3 at the second test site. The same combinations of AB diamond antibody and AB circle antibody used in generating the graph 410 where then used to generate data using the procedure 130 of FIG. 7 with a temperature difference between the two test sites. The results obtained from the simulation scenario are shown in graph 420 of FIG. 12.

Figure 4:
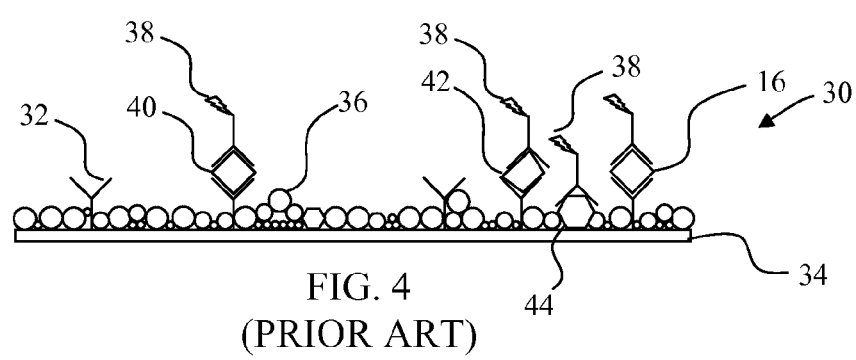
FIG. 4 depicts a schematic of a prior art test site within an ELISA array wherein a labeled secondary is bound to interfering molecules due to cross-reactivity and also physiosorbed to the surface of the substrate raising the background noise level of the test.
Figure 12:
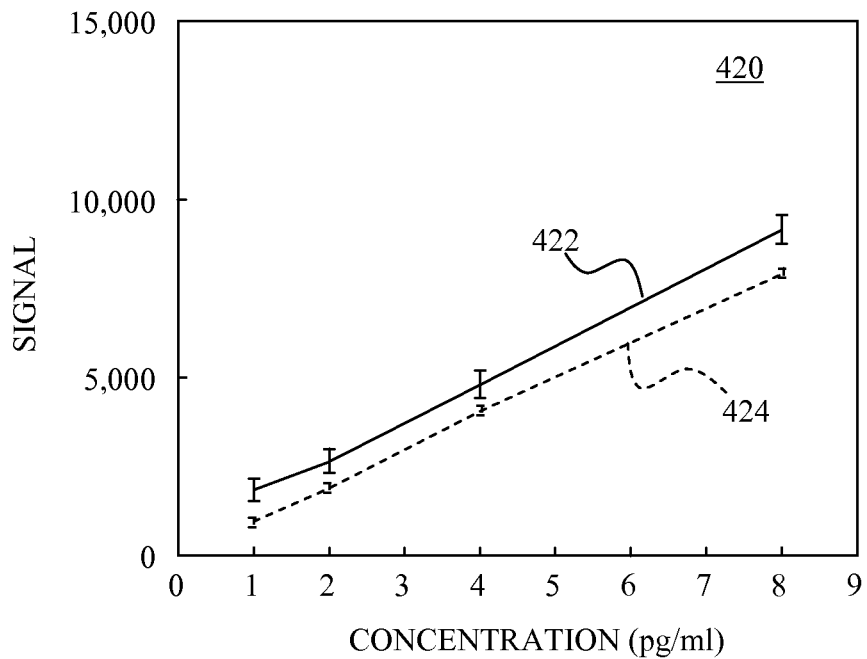
FIG. 12 depicts a graph of the calculated signal contribution from the molecule of interest in a number of samples after correcting for the increased signal resulting from another molecule using the procedure of FIG. 7.

In FIG. 12, the computed detected signal based upon the procedure 130 resulting from the AB diamond antibody is depicted as line 422. The signal based upon pure AB diamond antibody that was shown in FIG. 4 is depicted as line 424. A comparison of the slope of the lines 422 and 424 show a good correlation between the derived signal (line 422) and the actual signal (line 424) with less than 10% variation.

Figure 7:
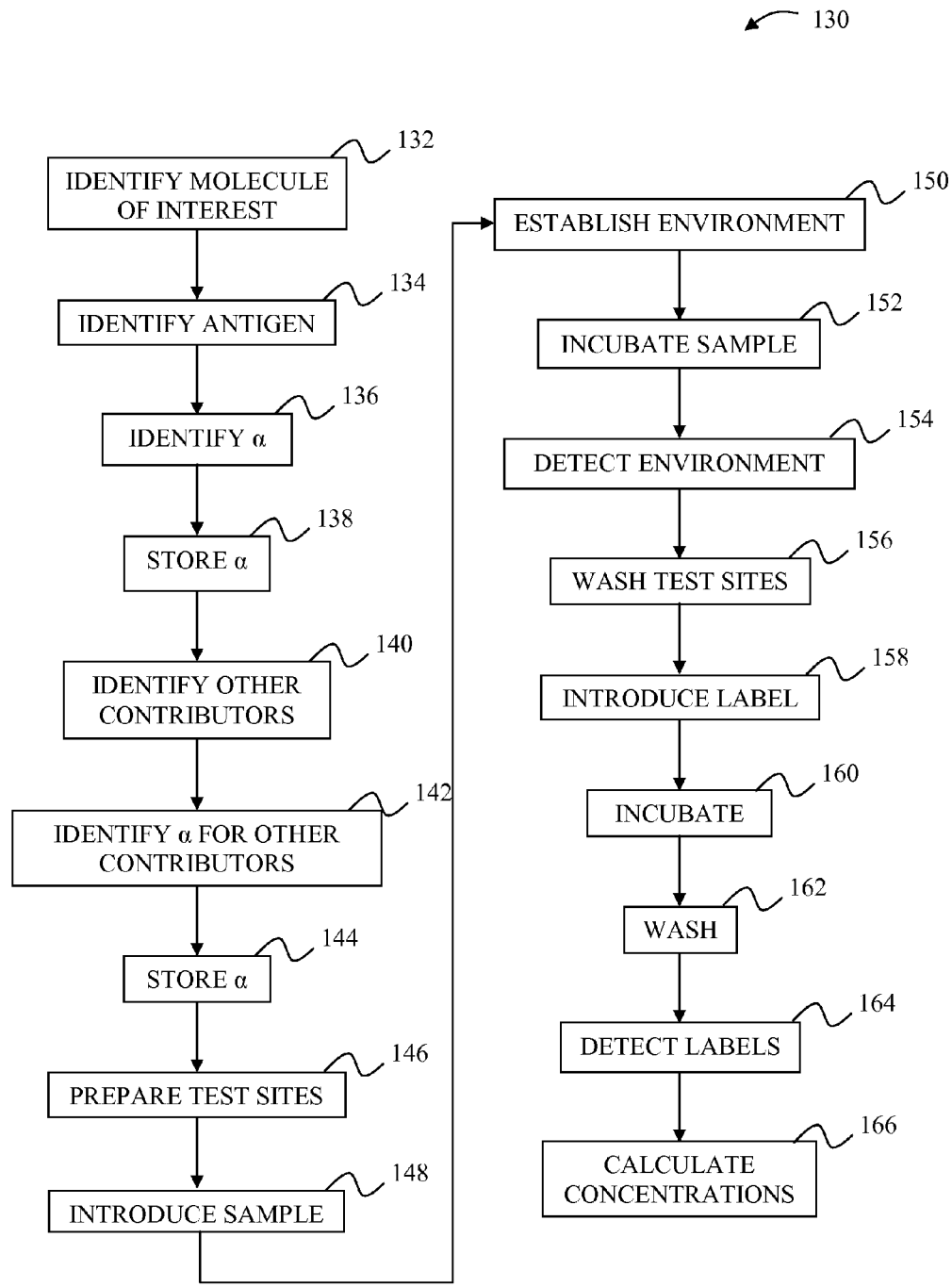
FIG. 7 depicts a procedure that can be used to establish different test environments at various test sites on a platform so as to expose a sample to multiple test environments.

The procedure 130 of FIG. 7 was also verified experimentally by using the calculations therein to predict a combined signal obtained from combinations of different antibodies at different temperatures. In this experiment, test sites on a streptavidin plate with rabbit pAb, mouse mAb, and biotin were exposed to different temperatures. One test site was established at 23° C. and a second test site was established at 47° C. The increased temperature resulted in increased binding efficiencies for the pAb, mAb, and biotin of 2.5×, 1.9×, and 1×, respectively.

Figure 13:
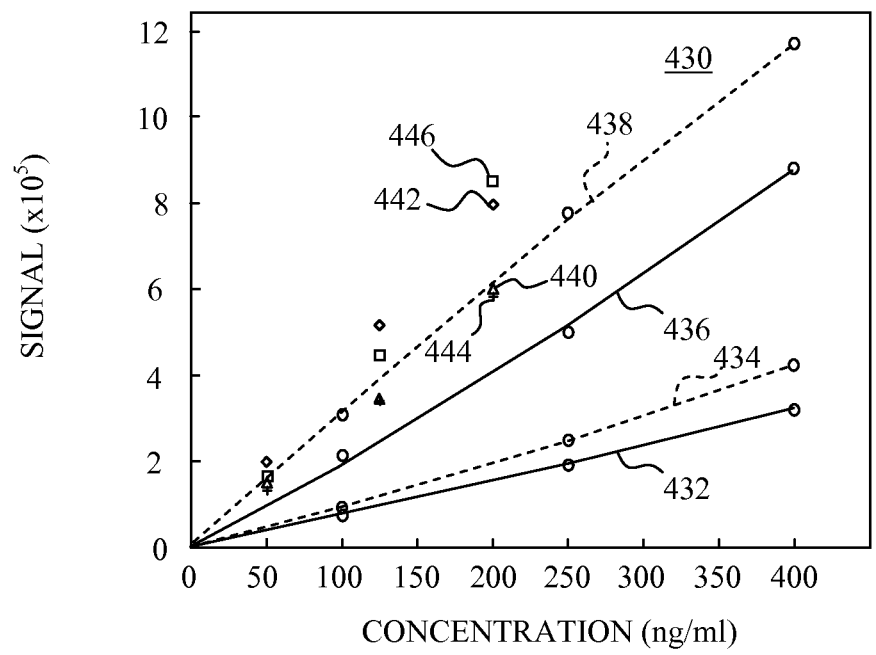
FIG. 13 depicts a graph of the detected signal resulting from samples of two different antibodies at two different temperatures along with the predicted and measured signal resulting from a sample including two antibodies.

The detected signal resulting from differing concentrations of the pAb, and mAb antibodies are depicted in graph 430 of FIG. 13. In FIG. 13, the line 432 depicts the detected signal from pure samples of pAb at 23° C. and the line 434 depicts the detected signal from pure samples of pAb at 47° C. Additionally, the line 436 depicts the detected signal obtained from pure samples of mAb at 23° C. and the line 438 depicts the detected signal from pure samples of mAb at 47° C.

The calculations described above with respect to the procedure 130 of FIG. 7 were then used to predict the signal that would be detected for a sample including both pAb and mAb at both of the test sites. In FIG. 13, the triangles 440 depict the predicted signal that would be obtained from samples of pAb/mAb mixed at a 1:1 ratio at 23° C. and the diamonds 442 depict the predicted signal that would be obtained from samples of pAb/mAb mixed at a 1:1 ratio at 47° C. based upon the procedure 130.

The experiment was then conducted with the pAb and mAb combined in a 1:1 ratio and the signal was obtained for various concentrations. In FIG. 13, the plus signs (+) 444 depict the experimental signal obtained from mixed samples of pAb/mAb at 23° C. and the squares 446 depict the experimental signal obtained from mixed samples of pAb/mAb at 47° C. FIG. 13 indicates that a good correlation between the slopes of the predicted signals and the experimental signals was realized.

Figure 14:
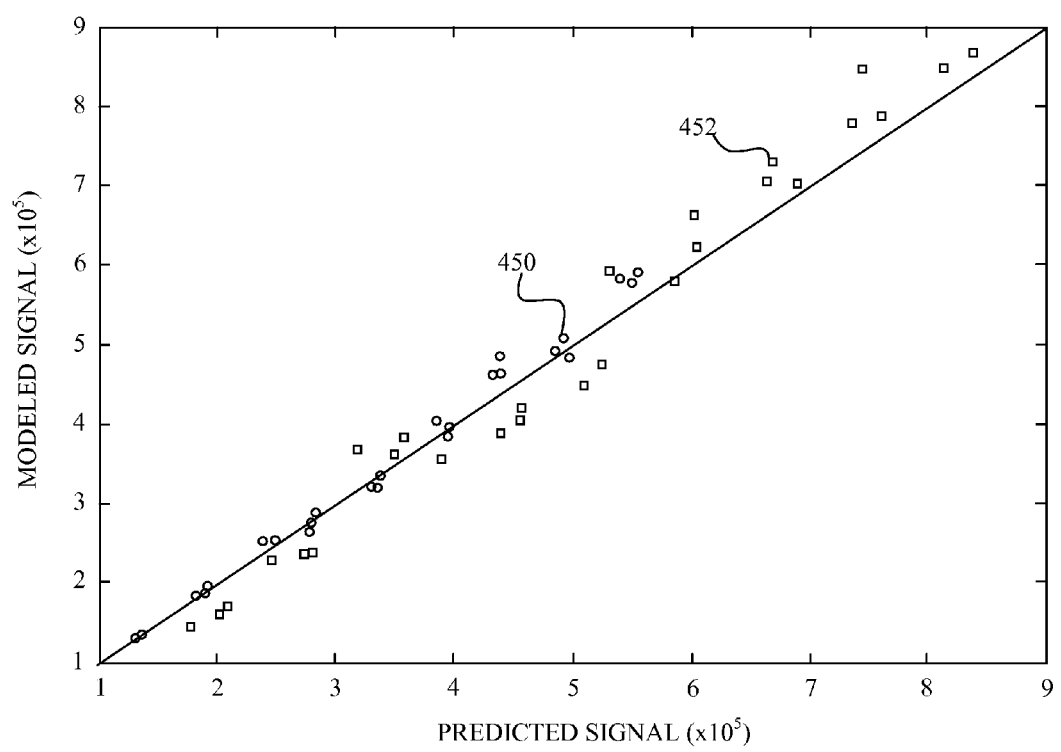
FIG. 14 depicts a graph of the correlation between the predicted and measured signals resulting from a sample including both of the antibodies of FIG. 13.

A further comparison of experimental versus predicted signals is provided in FIG. 14. In FIG. 14, the data points depicted as circles 450 show the correlation between the predicted signal and the experimental signal for mixed samples of pAb/mAb at 23° C. and the squares 452 depict the correlation between the predicted signal and the experimental signal for mixed samples of pAb/mAb at 47° C.

The concentration of a molecule of interest can thus be obtained even in the presence of other antibodies which generate an increase in the detected signal of a label. The background noise for a particular assay may also significantly increase the detected signal. Various advanced detection and control processes may be used to reduce or eliminate such background noise to increase the sensitivity of the procedure 130.

The procedure 130 can thus be used in a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays or other appropriate platforms. The procedure 130 may further be used for the detection of a variety of molecules of interest as well as different types of molecules in addition to antibodies. By way of example, the procedure 130 may also be used for the detection of Nucleic Acid, protein, or small molecules.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:
1. A method of detecting a biomarker comprising:
identifying a number of biomolecule types in a sample with an unknown concentration of the biomolecule types and at least two biomolecule types;
exposing the sample to a plurality of test sites, wherein the number of test sites in the plurality of test sites is based upon the identified number of biomolecule types so as to be equal to or greater than the identified number of biomolecule types;
establishing, for each of the plurality of test sites, a respective test environment, wherein the test environment for each of the plurality of test sites is different from the test environment for each of the other of the plurality of test sites, and each of the plurality of test sites is configured to capture each of the biomolecule types;

identifying, for each of the identified biomolecule types, a binding efficiency for each of the test environments for each of the plurality of test sites;

obtaining a detection signal associated with each of the plurality of test sites; and calculating the concentration of one of the biomolecule types based upon the obtained detection signals and the identified binding efficiencies.

2. The method of claim 1, wherein calculating the concentration comprises:

applying at least one linear estimation algorithm to the obtained detection signals.

3. The method of claim 1, wherein establishing a respective test environment comprises:

controlling at least one environmental factor of a group of environmental factors consisting of temperature, electric field, magnetic field, pH, and buffer type for each of the plurality of test sites, such that the controlled at least one environmental factor is different between at least two of the plurality of test sites.

4. The method of claim 3, wherein controlling at least one environmental factor comprises:

controlling the at least one environmental factor such that the controlled at least one environmental factor at each of the plurality of sites is different from each of the other of the plurality of test sites.

5. The method of claim 1, wherein establishing a respective test environment comprises:

providing at least one capturing agent;

identifying, for each of the plurality of test sites, a respective capturing agent recipe, wherein the capturing agent recipe for each of the plurality of test sites is different from the capturing agent recipe for each of the other of the plurality of test sites; and immobilizing, in each of the plurality of test sites, the at least one capturing agent in accordance with the identified recipe.

6. The method of claim 5, wherein the at least one capturing agent comprises a plurality of capturing agents, each of the plurality of capturing agents exhibiting an affinity to one or more of the identified biomolecule types that is different from the affinity to the one or more of the identified biomolecule types of another of the plurality of capturing agents.

7. The method of claim 6, wherein the capturing agent recipe for each of the plurality of test sites includes a selected one of the at least one capturing agent that is different from the at least one capturing agent in the other of the plurality of test sites.

8. The method of claim 5, wherein the capturing agent recipe for a first of the plurality of test sites includes a selected one of the at least one capturing agent that is the same as the at least one capturing agent in a second of the plurality of test sites.

9. The method of claim 8, wherein the concentration of the selected one of the at least one capturing agent in the first of the plurality of test sites is greater than the concentration of the selected one of the at least one capturing agent in the second of the plurality of test sites.

10. The method of claim 1, further comprising:

forming each of the plurality of test sites in a respective well of a multi-well plate.

11. The method of claim 1, further comprising:

forming each of the plurality of test sites on a CMOS substrate.

12. A method of determining a concentration of a biomarker in a sample comprising:

identifying a number of detection signal contributors for a plurality of detection signals, wherein at least one of the detection signal contributors is a molecule of interest;

exposing a sample with an unknown concentration of the molecule of interest to a plurality of test sites, wherein the number of test sites in the plurality of test sites is based upon the identified number of detection signal contributors so as to be equal to or greater than the identified number of detection signal contributors and each of the plurality of test sites is configured to capture each of the detection signal contributors;

establishing, for each of the plurality of test sites, a respective test environment, wherein the test environment for each of the plurality of test sites is different from the test environment for each of the other of the plurality of test sites;

identifying, for each of the detection signal contributors, a binding efficiency for each of the test environments for each of the plurality of test sites;

obtaining a respective one of the plurality of detection signals from each of the plurality of test sites; and calculating the concentration of the molecule of interest based upon the obtained plurality of detection signals and the identified binding efficiencies.

13. The method of claim 12, wherein establishing a respective test environment comprises:

controlling at least one environmental factor of a group of environmental factors consisting of temperature, electric field, magnetic field, and pH, for each of the plurality of test sites, such that the controlled at least one environmental factor is different between at least two of the plurality of test sites.

14. The method of claim 13, wherein controlling at least one environmental factor comprises:

controlling the at least one environmental factor such that the controlled at least one environmental factor at each of the plurality of sites is different from each of the other of the plurality of test sites.

15. The method of claim 12, wherein establishing a respective test environment comprises:

providing at least one capturing agent;

identifying, for each of the plurality of test sites, a respective capturing agent recipe, wherein the capturing agent recipe for each of the plurality of test sites is different from the capturing agent recipe for each of the other of the plurality of test sites; and immobilizing, in each of the plurality of test sites, the at least one capturing agent in accordance with the identified recipe.

16. The method of claim 15, wherein the at least one capturing agent comprises a plurality of capturing agents, each of the plurality of capturing agents exhibiting an affinity to one or more of the identified biomolecule types that is different from the affinity to the one or more of the identified biomolecule types of another of the plurality of capturing agents.

17. The method of claim 2, wherein calculating the concentration of one of the biomolecule types based upon the obtained detection signals comprises:

calculating the concentration of one of the biomolecule types based upon the following equations:

$$S_1 = \alpha_{1\text{-}1} C_1 + \alpha_{1\text{-}2} C_2$$

$$S_2 = \alpha_{2\text{-}1} C_1 + \alpha_{2\text{-}2} C_2$$

wherein
- $S_1$ is a first obtained signal associated with a first test site of the plurality of test sites,
- $S_2$ is a second obtained signal associated with a second test site of the plurality of test sites,
- $\alpha_{1\text{-}1}$ is a binding efficiency proportional to an affinity for a first of the identified at least two biomolecule types at the environment established in the first test site,
- $\alpha_{1\text{-}2}$ is a binding efficiency proportional to an affinity for a second of the identified at least two biomolecule types at the environment established in the first test site,
- $\alpha_{2\text{-}1}$ is a binding efficiency proportional to an affinity for the first of the identified at least two biomolecule types at the environment established in the second test site,
- $\alpha_{2\text{-}2}$ is a binding efficiency proportional to an affinity for the second of the identified at least two biomolecule types at the environment established in the second test site,
- $C_1$ is a concentration in the sample of the first of the identified at least two biomolecule types, and
- $C_2$ is a concentration in the sample of the second of the identified at least two biomolecule types.

18. The method of claim 1, wherein calculating the concentration of one of the biomolecule types based upon the obtained detection signals does not include:
  calculating a respective concentration with each of the obtained detection signals.

* * * * *